(12) United States Patent
Komiya et al.

(10) Patent No.: US 9,102,696 B2
(45) Date of Patent: Aug. 11, 2015

(54) PHOSPHORUS-BASED (METH)ACRYLATE COMPOUND AND METHOD OF PREPARING THE SAME

(71) Applicant: SANKO CO., LTD., Fukuoka (JP)

(72) Inventors: Naoki Komiya, Osaka (JP); Akira Inoue, Osaka (JP)

(73) Assignee: SANKO CO., LTD., Fukuoka (JP)

( * ) Notice: Subject to any disclaimer, the term of this patent is extended or adjusted under 35 U.S.C. 154(b) by 73 days.

(21) Appl. No.: 14/166,230

(22) Filed: Jan. 28, 2014

(65) Prior Publication Data

US 2014/0235886 A1    Aug. 21, 2014

(30) Foreign Application Priority Data

Feb. 15, 2013 (JP) .................................. 2013-028169

(51) Int. Cl.
*C07F 9/6571* (2006.01)

(52) U.S. Cl.
CPC ............................... *C07F 9/657172* (2013.01)

(58) Field of Classification Search
CPC ................................................ C07F 9/657172
See application file for complete search history.

(56) References Cited

U.S. PATENT DOCUMENTS 5,453,452 A    9/1995 Nakayama et al.

FOREIGN PATENT DOCUMENTS

| JP | 05-058950 | | 3/1993 |
|---|---|---|---|
| JP | 2002-020433 | | 1/2002 |
| JP | 2008303260 | * | 12/2008 |
| TW | 201206951 A1 | * | 2/2012 |
| WO | WO 2013/114866 | * | 8/2013 |

* cited by examiner

*Primary Examiner* — Valerie Rodriguez-Garcia
(74) *Attorney, Agent, or Firm* — Hamre, Schumann, Mueller & Larson, P.C.

(57) ABSTRACT

This invention relates to a novel compound having high refractive index suitable for use in optical resin materials, etc., without containing a sulfur atom, and to a method of preparing the same, in which the compound is a phosphorus-based (meth)acrylate compound represented by Formula (I).

4 Claims, 3 Drawing Sheets

PHOSPHORUS-BASED (METH)ACRYLATE COMPOUND AND METHOD OF PREPARING THE SAME

CROSS REFERENCE TO RELATED APPLICATION

This application claims the benefit of Japanese Patent Application No. JP 2013-028169. filed Feb. 15, 2013, which is hereby incorporated by reference in its entirety into this application.

BACKGROUND OF THE INVENTION

1. Technical Field

The present invention relates to a novel phosphorus-based (meth)acrylate compound and a method of preparing the same.

2. Description of the Related Art (Meth)acrylic resins including polymethyl methacrylate are variously utilized in optical materials, etc. because of transparency thereof. However, typical (meth)acrylic resins are not sufficiently high in refractive index, and thus are difficult for use in end uses requiring high refractive index. Hence, novel materials having higher refractive index are required.

With regard thereto, disclosed as (meth)acrylate having high refractive index is an acrylate having a benzene ring backbone (Patent Document 1). The refractive index thereof is about 1.58, which is higher than the refractive index of current (meth)acrylic resins, including polymethyl methacrylate.

Also, in order to increase the refractive index of a resin material, a method of introducing a sulfur atom having high polarizability into a molecule is disclosed (Patent Document 2).

CITATION LIST

Patent Literature (Patent Document 1) Japanese Patent Application Publication No. 1993-58950
(Patent Document 2) Japanese Patent Application Publication No. 2002-20433

SUMMARY OF THE INVENTION

However, the refractive index of the acryate disclosed in Patent Document 1 is regarded as not being sufficiently high in recent years.

Furthermore, the resin material disclosed in Patent Document 2 contains a :sulfur atom in the structure thereof, undesirably causing distinctive odor in the course of preparation thereof, etc.

Accordingly, the present invention has been made keeping in mind the above problems encountered in the related art, and an object of the present invention is to provide a novel compound having high refractive index adapted for use in optical resin materials, etc., without containing a sulfur atom, and a method of preparing the same.

In order to accomplish the above object, the present invention provides a phosphorus-based (meth)acrylate compound represented by Formula (I) below:

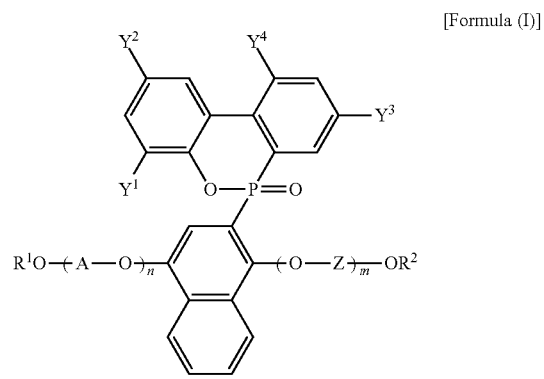

[Formula (I)]

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; n and in are each independently 0, 1 or 2, and when n or in is 2, two As or Zs are the same as or different from each other; and $R^1$ and $R^2$ are each independently a hydrogen atom or a (meth)acryloyl group, in which at least one of $R^1$ and R2 is a (meth)acryloyl group, In the present invention, the phosphorus-based (meth)acrylate compound is preferably represented by Formula (a) below.

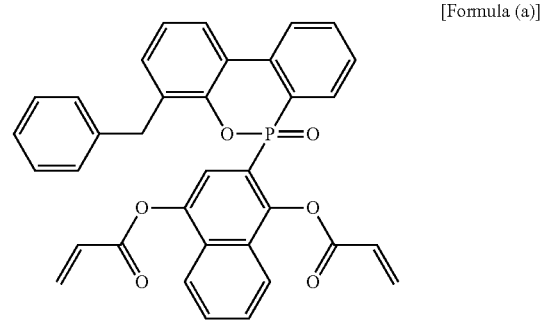 [SMILES: C=CC(=O)Oc1cc(P2(=O)Oc3c(Cc4ccccc4)cccc3-c3ccccc32)c(OC(=O)C=C)c2ccccc12]

[Formula (a)]

In the present invention, the phosphorus-based (meth)acrylate compound is preferably represented by Formula (b) below.

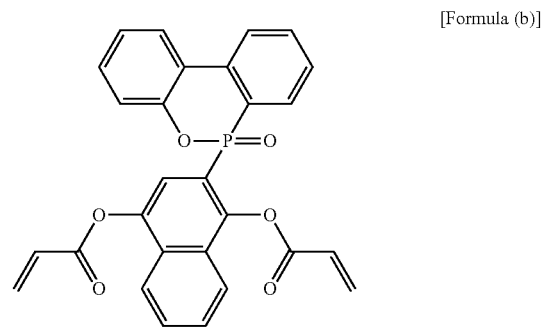 [SMILES: C=CC(=O)Oc1cc(P2(=O)Oc3ccccc3-c3ccccc32)c(OC(=O)C=C)c2ccccc12]

[Formula (b)]

In the present invention, the phosphorus-based (meth)acrylate compound is preferably represented by Formula (c) below.

[Formula (c)]

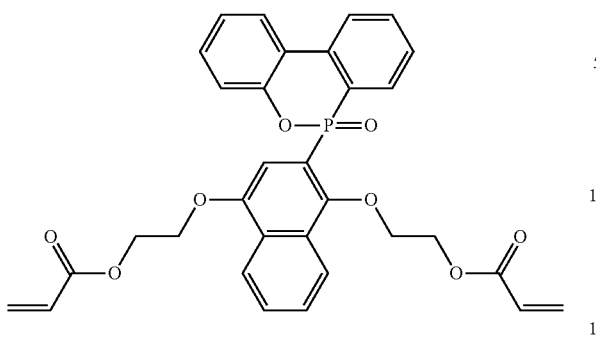

In addition, the present invention provides a method of preparing a phosphorus-based (meth)acrylate compound represented by Formula (I)-1 below, including reacting a compound represented by Formula (III) below with one or more selected from the group consisting of (meth)acrylic acid, (meth)acrylic acid chloride and di(meth)acrylic acid anhydride to give a phosphorus-based (meth)acrylate compound represented b Formula (I)-1 below:

[Formula (III)]

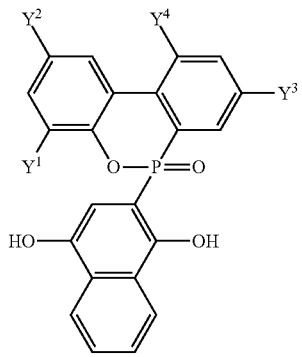

[Formula (I)-1]

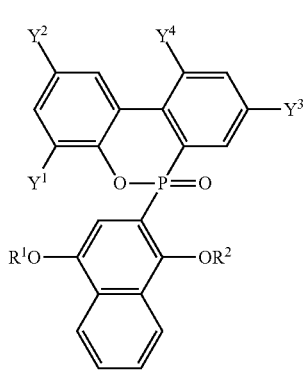

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group, and $R^1$ and $R^2$ are each independently a hydrogen atom or a (meth)acryloyl group, in which at least one of $R^1$ and $R^2$ is a (meth)acryloyl group.

In addition, the present invention provides a method of preparing a phosphorus-based (meth)acrylate compound represented by Formula (I)-2 below, including reacting a compound represented by Formula (III) below with one or more selected from the group consisting of ethylene oxide, ethylene carbonate, propylene oxide and propylene carbonate to give a compound represented by Formula (IV) below, and reacting the compound represented by Formula (IV) below with one or more selected from the group consisting of (meth)acrylic acid, (meth)acrylic acid chloride and di(meth)acrylic acid anhydride to give a phosphorus-based (meth)acrylate compound represented by Formula (I)-2 below:

[Formula (III)]

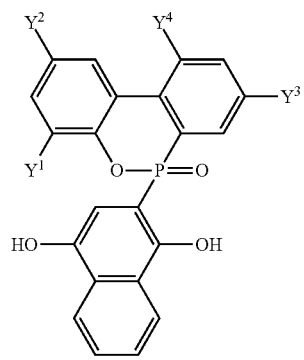

[Formula (IV)]

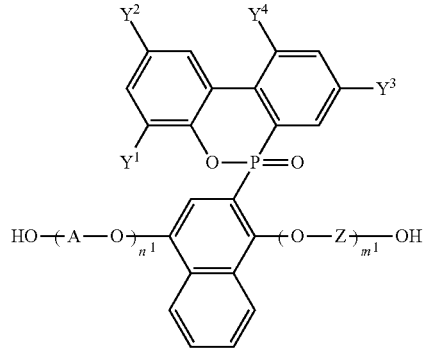

[Formula (I)-2]

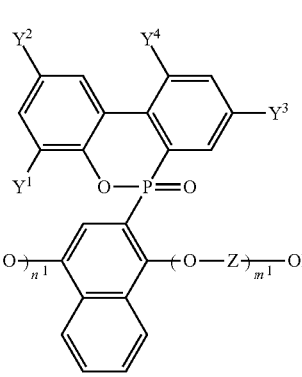

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; $n^1$ and $m^1$ are each independently 0, 1 or 2, in which both of $n^1$ and $m^1$ are not zero, and when $n^1$ or $m^1$ is 2. two As or Zs are the same as or different from each other; and $R^1$ and $R^2$ are each independently a hydrogen atom or a (meth)acryloyl group, in which at least one of $R^1$ and $R^2$ is a (meth)acryloyl group.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE SPECIFIC EMBODIMENTS

Figure 1:
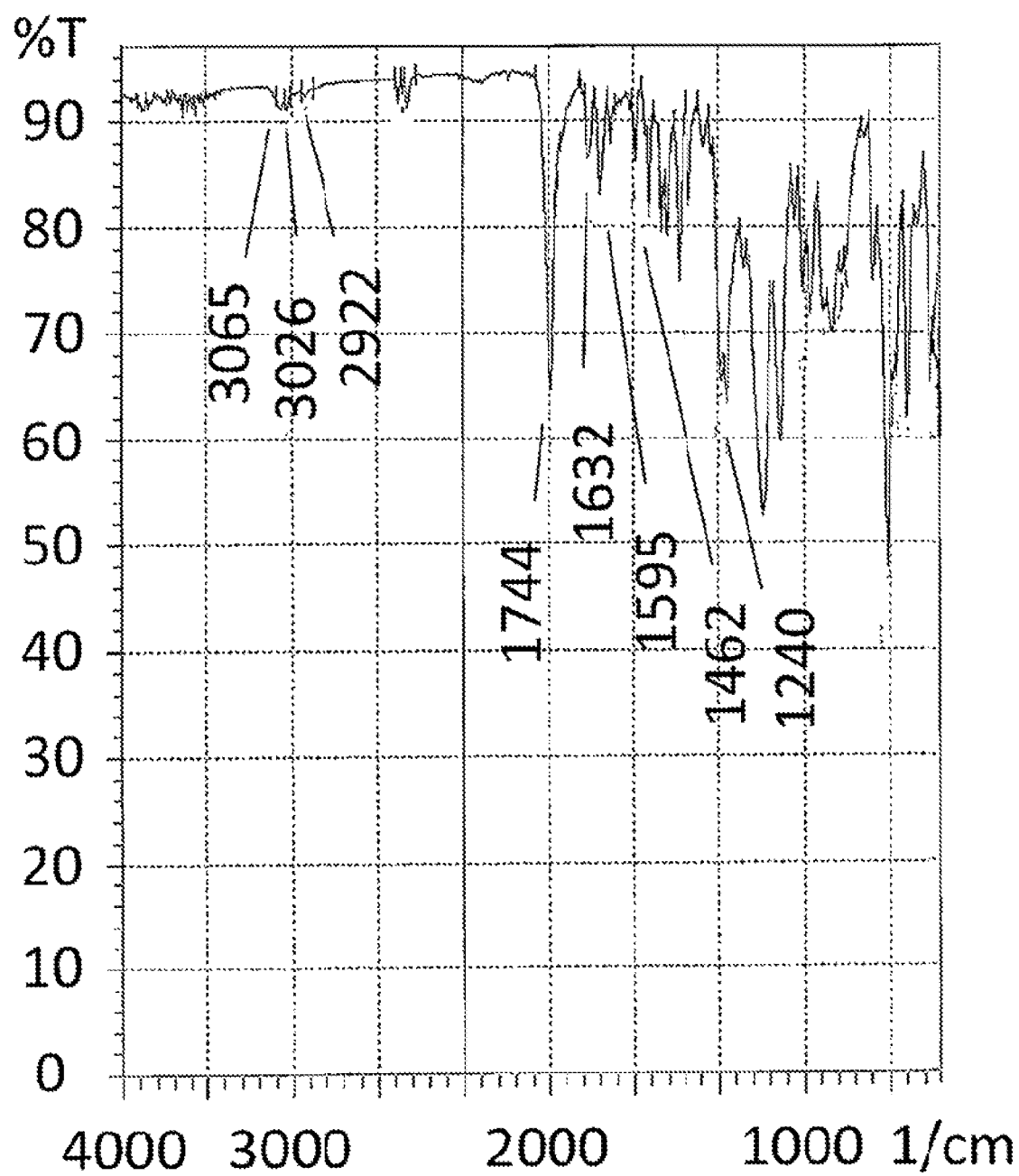
FIG. 1 illustrates infrared (IR) absorption spectrum data of Compound (a) obtained in Example 1.

In the present invention, a phosphorus-based (meth)acrylate compound is a dihydrooxaphosphophenanthrene derivative represented by Formula (I) below (hereinafter, referred to as "Compound (I)").

Compound (I), which is newly found as a compound having high refractive index without generating distinctive odor as in a compound containing a sulfur atom, is a novel compound having a dihydrooxaphosphophenanthrene backbone with a phosphorus atom and a (meth)acryloyl group.

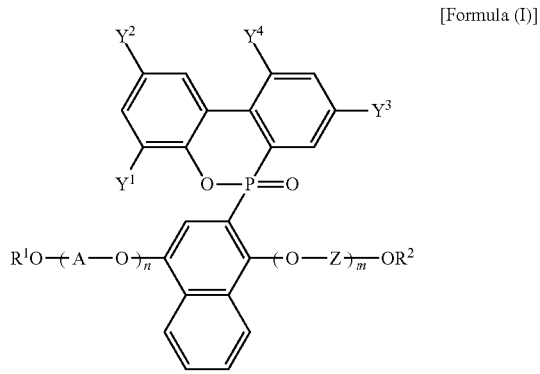

[Formula (I)]

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; n and m are each independently 0, 1 or 2, and when n or m is 2, two As or Zs are the same as or different from each other; and $R^1$ and $R^2$ are each independently a hydrogen atom or a (meth)acryloyl group, in which at least one of $R^1$ and $R^2$ is a (meth)acryloyl group.

In Formula (I), $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group (2-propenyl group). As such, all of $Y^1$ to $Y^4$ may be the same as or different from each other, and some of them may be the same as each other.

In $Y^1$ to $Y^4$, examples of the halogen atom may include a fluorine atom, a chlorine atom, a bromine atom, and an iodine atom.

In $Y^1$ to $Y^4$, the alkyl group may be linear, branched or cyclic, and it preferably has 1 to 10 carbon atoms.

The linear or branched alkyl group preferably has 1 to 10 carbon atoms, and examples thereof may include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, and a decyl group.

The cyclic alkyl group may be either monocyclic or polycyclic. In the case of a polycyclic alkyl group, the number of rings is not particularly limited so long as it is 2 or more.

The cyclic alkyl group preferably has 3 to 10 carbon atoms, and examples thereof may include a cyclopropyl group, a cyclobutyl group, a cyclopentyl group, a cyclohexyl group, a cycloheptyl group, a cyclooctyl group, a cyclononyl group, a cyclodecyl group, norbornyl group, an isobornyl group, a 1-adamantyl group, a 2-adamantyl group, and a tricyclodecyl group, and also may include those in which one or more hydrogen atoms of the cyclic alkyl group are substituted with a linear, branched or cyclic alkyl group. As such, the linear, branched or cyclic alkyl group used to replace the hydrogen atom may include those exemplified as above.

In $Y^1$ to $Y^4$, the aryl group may be either monocyclic or polycyclic. In the case of a polycyclic aryl group, the number of rings is not particularly limited so long as it is 2 or more.

The aryl group preferably has 6 to 12 carbon atoms, and examples thereof may include a phenyl group, a 1-naphthyl group, a 2-naphthyl group, an o-tolyl group, a m-tolyl group, a p-tolyl group, a xylyl group (a dimethylphenyl group), etc., and may also include those wherein one or more hydrogen atoms of the aryl group are substituted with a linear, branched or cyclic alkyl, or aryl group. As such, the linear, branched or cyclic alkyl, or aryl group used to replace the hydrogen atom may include those exemplified as above.

In $Y^1$ to $Y^4$, examples of the aralkyl group may include a benzyl group (a phenylethyl group), a 1-methylbenzyl group, a phenylethyl group (a phenylethyl group), etc., as groups wherein one hydrogen atom of the alkyl group in $Y^1$ to $Y^4$ is substituted with the aryl group in $Y^1$ to $Y^4$.

In $Y^1$ to $Y^4$, the aralkyl group preferably has 7 to 22 carbon atoms, and more preferably 7 to 12 carbon atoms.

In $Y^1$ to $Y^4$, examples of the acyl group may include a formyl group, an acetyl group, a benzoyl group, a 1-naphthoyl group, a 2-naphthoyl group, etc., as monovalent groups formed by linking a hydrogen atom or the alkyl, aryl or aralkyl group in $Y^1$ to $Y^4$ to the carbon atom of a carbonyl group (—C(=O)—).

In $Y^1$ to $Y^4$ the acyl group preferably has 1 to 23 carbon atoms, and more preferably 1 to 13 carbon atoms.

In the above formula, A and Z are each independently an ethylene group (—CH$_2$CH$_2$—) or an isopropylene group (—CH(CH$_3$)CH$_2$—).

In the above formula, n and in are each independently 0, 1 or 2.

When n is 2, two As are the same as or different from each other, and when m is 2, two Zs are the same as or different from each other.

In the above formula, $R^1$ and $R^2$ are each independently a hydrogen atom or a (meth)acryloyl group, in which at least one of $R^1$ an $R^2$ is a (meth)acryloyl group.

As used herein, the term "(meth)acryloyl group" refers to a concept including both of an acryloyl group and a methacryloyl group.

Preferable examples of Compound (I) include compounds represented by Formulas (a), (b) and (c) below (hereinafter, which are respectively referred to as "Compound (a)", "Compound (b)" and "Compound (c)").

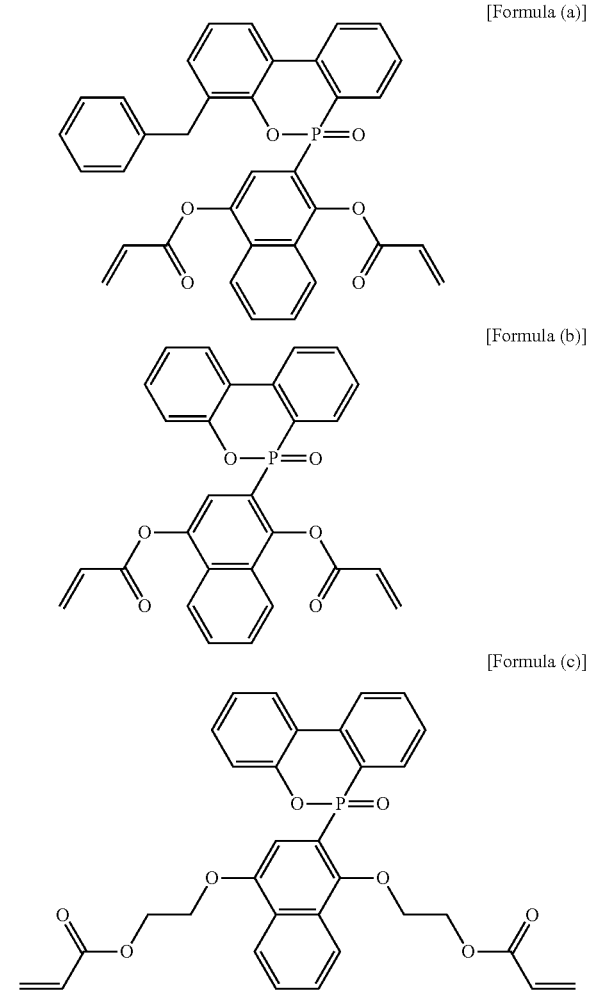

Compound (I) having a phosphorus atom in the structure thereof is high in polarizability and has high refractive index, and preferably, the refractive index thereof is set to 1.60 or more. Also, Compound (I), due to having high refractive index, may be suitable for use in optical resin materials, etc., for example, materials for liquid crystal display panels, color filters, glasses lenses, Fresnel lenses, lenticular lenses, prism lens sheets for TFTs, optical fibers, optical disks, etc. Furthermore, Compound (I), due to having a phosphorus atom in the structure thereof, is adapted for use in resin materials requiring distinctive flame retardancy or high adhesion to a substrate (see Japanese Patent Application Publication No. 2002-506480 and Japanese Patent Application Publication No. 2007-231107).

Also, Compound (I) contains no sulfur atom in the structure thereof, and thus generates no distinctive odor in the course of the preparation thereof, etc.

Compound (I) may be prepared by the following method depending on for example whether each of n and in are zero.

Among Compound (I), a compound represented by Formula (I)-1 below (hereinafter, referred to as "Compound (I)-1") corresponding to the case that n=m=0 may be prepared by a method having a process of reacting a compound represented by Formula (III) below (hereinafter, referred to as "Compound (III)") with one or more selected from the group consisting of (meth)acrylic acid, (meth)acrylic acid chloride and di(meth)acrylic acid anhydride to give a phosphorus-based (meth)acrylate compound represented by Formula (1)-1 below (Compound (I)-1):

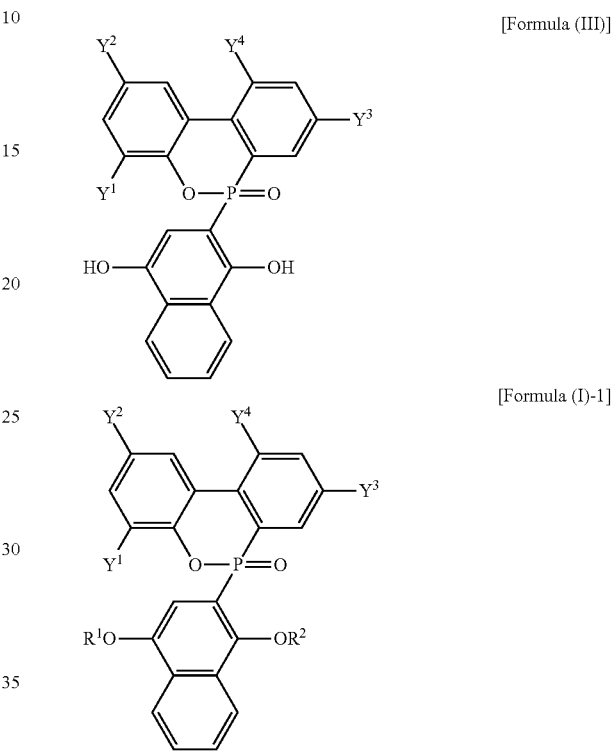

wherein $Y^1, Y^2, Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group, and $R^1$ and $R^2$ are each independently a hydrogen atom or a (meth)acryloyl group, in which at least one of $R^1$ and $R^2$ is a (meth)acryloyl group.

In Formulas (III) and (I)-1, $Y^1, Y^2, Y^3, Y^4, R^1$ and $R^2$ are the same as $Y^1, Y^2, Y^3, Y^4, R^1$ and $R^2$ in Formula (I).

In the preparation of Compound (I)-1, the reaction of Compound (III) and one or more selected from the group consisting of (meth)acrylic acid, (meth)acrylic acid chloride and di(meth)acrylic acid anhydride is preferably carried out by dissolving at least one of them in an organic solvent. Also, this reaction may be implemented in the presence or absence of a catalyst.

The total amount of one or more selected from the group consisting of (meth)acrylic acid, (meth)acrylic acid chloride and di(meth)acrylic acid anhydride is preferably set to a molar amount 2~6 times, and more preferably 2~4 times the molar amount of Compound (III).

In the preparation of Compound (I)-1, the organic solvent is not particularly limited but preferable examples thereof include ester such as methyl acetate, ethyl acetate, phenyl acetate, benzyl acetate, etc.; halogenated hydrocarbon such as dichloromethane, trichloromethane, etc.; ketone such as methylisobutylketone, etc.; ether such as tetrahydrofuran, etc.; aromatic hydrocarbon such as benzene, toluene, xylene, etc.; aromatic alcohol such as phenol, etc.; and amide such as N,N-dimethylformamide (DMF), N,N-dimethylacetamide (DMAc), etc.

The above organic solvent may be used alone or in combination of two or more.

In the preparation of Compound (I)-1. the catalyst is preferably appropriately adopted depending on the type of other material used. Furthermore, the catalyst may be used alone or in combination of two or more.

For example, in the case of using (meth)acrylic acid, an acid catalyst is preferably used. The acid catalyst is not particularly limited, but examples thereof preferably include an inorganic acid such as hydrochloric acid, sulfuric acid, etc.; an organic acid such as acetic acid, p-toluenesulfonic acid, methanesulfonic acid, trifluoromethanesulfonic acid, etc., and the like.

In the case of using (meth)acrylic acid chloride, a base catalyst is preferably used. The base catalyst is not particularly limited, but preferable examples thereof include, when it is an organic base, a nitrogen-containing aliphatic compound such as triethylamine, diethylamine, etc.; a nitrogen-containing aromatic heterocyclic compound such as pyridine, pyrimidine, etc., when it is an inorganic base, carbonate or hydrogen carbonate such as sodium carbonate, sodium hydrogen carbonate, etc., and the like.

In the case of using di(Meth)acrylic acid anhydride, an ester catalyst, an acid catalyst, a base catalyst, or a Lewis acid catalyst may be used. The ester catalyst may be exemplified by a salt of alkali metal such as sodium, potassium, etc. of lower carbonic acid, such as sodium acetate, potassium propionate, sodium (meth)acrylate, etc. The acid catalyst may be exemplified by an inorganic acid such as sulfuric acid, boric acid, etc.; an organic acid such as methanesulfonic acid, p-toluenesulfonic acid, etc, and the like. Also, when the base catalyst is an organic base, it may be exemplified by a nitrogen-containing aliphatic compound such as triethylamine, triethylenediamine, etc.; a nitrogen-containing aromatic heterocyclic compound such as pyridine, etc., and the like. Also, the Lewis acid catalyst may be exemplified by aluminum chloride, zinc chloride, etc.

In the preparation of Compound (I)-1, the reaction may be carried out in the presence of a polymerization inhibitor such as p-methoxyphenol, hydroquinone, etc., as necessary.

In the preparation of Compound (I)-1, the reaction temperature is preferably set to –25~150° C. More preferably, the reaction temperature is set to –25~100° C. because probability of generating polymerization upon reaction at high temperature may increase. Furthermore, the reaction time is preferably adjusted depending on the reaction temperature, and is preferably set to 1~15 hr.

In the preparation of Compound (I)-1, after termination of the reaction, post-treatment is performed using a known method, as necessary, in consideration of the properties of Compound (I)-1, kind and amount of material or catalyst used, use or not use of the organic solvent, etc., Whereby Compound (I)-1 is obtained. Specifically, post-treatment processes such as filtration, cleaning, extraction, pH adjusting, dewatering, concentrating, etc. may be appropriately conducted alone or in combination of two or more, as necessary, and thereby Compound (I)-1 is obtained through concentrating, crystallization, reprecipitation column chromatography, etc. Also, Compound (I)-1 thus obtained may be purified in such a manner that crystallization, reprecipitation, column chromatography, extraction, stirring and cleaning of crystals by the solvent, etc. alone or in combination of two or more may be performed once or more, as necessary.

In addition, Compound (III) may be prepared by a known method as disclosed in, for example, Japanese Patent Application Publication No. Sho. 61-236787, such as a method including reacting a compound represented by Formula (II) below (hereinafter, referred to as "Compound (II)") with 1,4-naphthoquinone.

For example, in the reaction of Compound (II) and 1,4-naphthoquinone, a solution of Compound (II) in an inert organic. solvent such as ethyleneglycol lower alkylether propyleneglycol lower alkylether, benzene or toluene, etc. is prepared, so that the amount of Compound (II) is adjusted to exceed the amount of 1,4-naphtoquinone, and 1,4-naphtoquinone is preferably added in a micropowder phase or in the form of the same inert organic solvent solution as above, after which the resulting mixture is preferably reacted at 60~150° C. for 0.5~5 hr and more preferably 70~120° C. for 1.5~3 hr, cooled to about room temperature to deposit crystals, which are then filtered, cleaned and dried, yielding Compound (III). The method of preparing Compound (III) is not limited thereto.

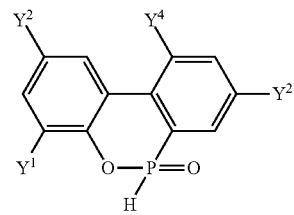

[Formula (II)]

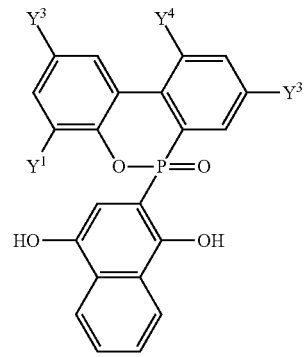

[Formula (III)]

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group.

In Formula (II), $Y^1$, $Y^2$, $Y^3$ and $Y^4$ are the same as $Y^1$, $Y^2$, $Y^3$ and $V^4$ in Formula (I).

Also, useful as Compound (II) or (III) may be commercially available products. For example, commercially available products of Compound (II) may include a compound wherein all of $Y^1$, $Y^2$, $Y^3$ and $Y^4$ are a hydrogen atom (9,10-dihydro-9-oxa-10-phosphophenanthrene-10-oxide, "HCA" available from Sanko), a compound wherein $Y^1$ is a benzyl group and all of $Y^2$, $Y^3$ and $Y^4$ are a hydrogen atom (8-benzyl-9,10-dihydro-9-oxa-10-phosphophenanthrene-10-oxide, "Bz-HCA" available from Sanko), etc. Furthermore, commercially available products of Compound (III) may include a compound wherein all of $Y^1$, $Y^2$, $Y^3$ and $Y^4$ are a hydrogen atom (9,10-dihydro-10-(2,7-dihydroxynaphthyl)-9-oxa-10 -phosphophenanthrene-10-oxide, "HCA-NQ" available from Sanko), a compound wherein $Y^1$ is a benzyl group and all of $Y^2$, $Y^3$ and $Y^4$ are a hydrogen atom (8-benzyl-9,10- dihydro-10-(2,7-dihydroxynaphthyl)-9-oxa-10-phosphophenanthrene-10-oxide, "Bz-HCA-NQ" available from Sanko), etc.

As for Compound (I), a compound represented by Formula (I)-2 below (hereinafter, referred to as "Compound (I)-2") corresponding to a compound except for the case where both of n and m are zero may be prepared by reacting Compound (III) with one or more selected from the group consisting of ethylene oxide, ethylene carbonate, propylene oxide and propylene carbonate to give a compound represented by Formula (IV) below (hereinafter, referred to as "Compound (IV)") and reacting Compound (IV) with one or more selected from the group consisting of (meth)acrylic acid, (meth)acrylic acid chloride and di(meth)acrylic acid anhydride to give a phosphorus-based (meth)acrylate compound represented by Formula (I)-2 below (Compound (I)-2):

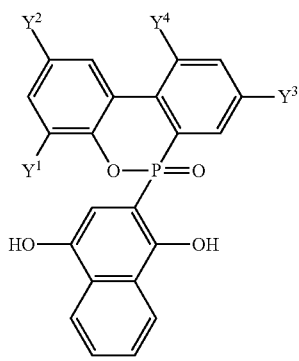

[Formula (III)]

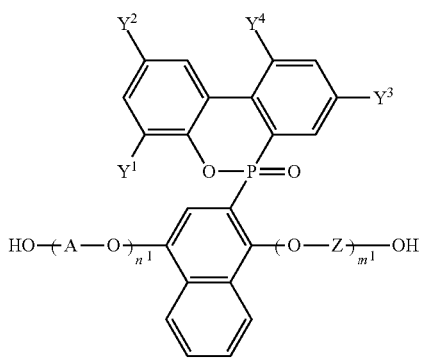

[Formula (IV)]

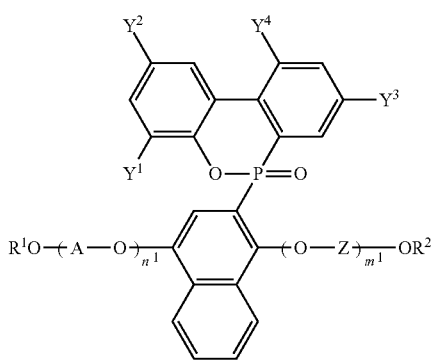

[Formula (I)-2]

wherein $Y^1$, $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; $n^1$ and $m^1$ are each independently 0, 1 or 2, in which both of $n^1$ and $m^1$ are not zero, and when $n^1$ or $m^1$ is 2, two As or Zs are the same as or different from each other; and $R^1$ and $R^2$ are each independently a hydrogen atom or a (meth)acryloyl group, in which at least one of $R^1$ and $R^2$ is a (meth)acryloyl group.

In Formulas (no and (I)-2, $Y^1$, $Y^2$, $Y^3$, $Y^4$, A, Z, $R^1$ and $R^2$ are the same as $Y^1$, $Y^2$, $Y^3$, $Y^4$, A, Z, $R^1$ and $R^2$ in Formula (I).

Also, in Formulas (IV) and (I)-2, $n^1$ and $m^1$ are each independently 0, 1 or 2, in which both of $n^1$ and $m^1$ are not zero (at the same time), and when $n^1$ is 2, two As are the same as or different from each other, and when $m^1$ is 2, two Zs are the same as or different from each other.

Below is a description of the case where both of $n^1$ and $m^1$ are not zero.

In this case, in the preparation of Compound (IV), the reaction of Compound (III) and one or more selected from the group consisting of ethylene oxide, ethylene carbonate, propylene oxide and propylene carbonate is preferably performed by dissolving at least one of them in an organic solvent. Furthermore, this reaction may be conducted in the presence or absence of a catalyst.

Ethylene oxide, ethylene carbonate, propylene oxide and propylene carbonate function to impart A and Z of Compound (IV).

The total amount of one or more selected from the group consisting of ethylene oxide, ethylene carbonate, propylene oxide and propylene carbonate is preferably set to a molar amount 2~6 times and more preferably 2~4 times the molar amount of Compound (III).

In the preparation of Compound (IV), the organic solvent may be the same as the organic solvent used in the preparation of Compound (I)-1.

In the preparation of Compound (IV), the catalyst is not particularly limited so long as it reacts with the other materials used and it does not inhibit the target reaction. The catalyst may be used alone or in combinations of two or more.

Preferable examples of the catalyst include an acid catalyst and a base catalyst.

Although the acid catalyst is not particularly limited, examples thereof preferably include an inorganic acid such as hydrochloric acid, sulfuric acid, etc.; an organic acid such as acetic acid, p-toluenesulfonic acid, methanesulfonic acid, etc, and the like.

Although the base catalyst is not particularly limited, examples thereof when it is an inorganic base, preferably include carbonate or hydrogen carbonate such as sodium carbonate, sodium hydrogen carbonate, potassium carbonate, potassium hydrogen carbonate, etc, and the like.

In the preparation of Compound (IV), the reaction temperature is preferably set to 100~180° C., and more preferably 140~160° C. Also, the reaction time is preferably adjusted depending on the reaction temperature, and is preferably set to 1~15 hr.

In the preparation of Compound (IV), after termination of the reaction, post-treatment is performed by a known method, as necessary, thus obtaining Compound (IV), as in the preparation of Compound (I)-1. Furthermore, appropriate post-treatment is performed as necessary, after which Compound (IV) is not obtained but the subsequent step (preparation of Compound (I)-2) may be performed.

Then, the case where only one of $n^1$ and $m^1$ is zero is described.

In this case, in the reaction for preparation of Compound (IV), the total amount of one or more (hereinafter, referred to as "ethylene oxide and so on") selected from the group consisting of ethylene oxide, ethylene carbonate, propylene oxide and propylene carbonate is preferably set to a molar amount less than 2 times, more preferably 0.8~1.8 times, and much more preferably 1~1.5 times the molar amount of Compound (III). In this way, the total amount of ethylene oxide and so on is reduced compared to the case where both of $n^1$ and $m^1$ are not zero, thereby improving the yield of desired Compound (IV). In addition to a method of reducing the total amount of ethylene oxide and so on to improve the yield of Compound (IV), there are exemplified a method of lowering the reaction temperature (e.g. the reaction temperature is preferably set to the range from 80° C. to less than 100° C.), a method of shortening the reaction time (e.g. the reaction time is preferably set to the range from 30 min to less than 1 hr). etc., compared to the case where both of $n^1$ and $m^1$ are not zero. Moreover, these methods may be used in combination of two or more. Preparation of Compound (IV) using these methods may be carried out in the same manner as in the case where both of $n^1$ and $m^1$ are not zero, with the exception that the reaction conditions are changed as above. When byproducts are generated, the above obtainment method or purification method may be appropriately applied, thus easily obtaining Compound (IV) as desired.

After preparation of Compound (IV), preparation of Compound (I)-2 is performed.

Preparation of Compound (I)-2 may be performed in the same manner as in the preparation of Compound (I)-1, with the exception that Compound (IV) is used instead of Compound (III). For example, after termination of the reaction, post-treatment is performed by a known method, as necessary, thus obtaining Compound (I)-2, and Compound (I)-2 thus obtained may be purified as necessary.

The method of preparing Compound (I) is excellent in terms of efficiently producing target compounds (Compounds (I)-1 and (I)-2).

EXAMPLES

A better understanding of the present invention may be obtained via the following examples which are set forth to illustrate, but are not to be construed as limiting the present invention.

<Preparation of Compound (I)>

Example 1

(Preparation of Compound (a))

[Formula (III)-101]

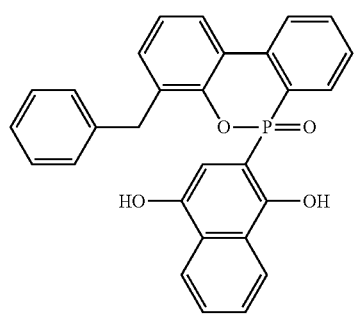

[Formula (a)]

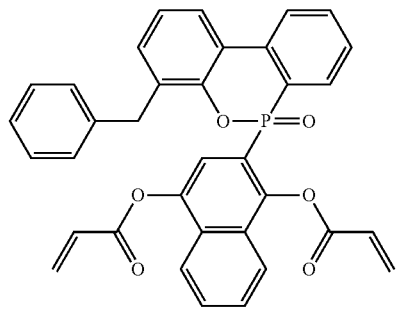

In a 1000 ml four-neck flask, Compound (III)-101 (Bz-HCA-NQ) (139.3 g, 0.30 mol) and ralAc (418.8 g, 5.2 mol) were placed and dissolved, after which acrylic acid chloride (81.9 g, 0.90 mol) having dissolved p-methoxyphenol (0.08 g, 0.006 mol) was added in a dropwise 1m-timer, and triethylamine (100.0 g, 0.99 mol) was added in a dropwise manner. Subsequently, the resulting mixture was reacted at 10° C. for 5 hrs. After termination of the reaction, the reaction solution was added into water. crystals were deposited, and the solvent was removed, thus obtaining crude crystals. The crude crystals thus obtained were dissolved in methylisobutylketone, followed by sequentially performing water washing, dewatering, decolorization and concentrating, and the resulting concentrate was added with seed crystals to thus deposit crystals, after which the crystals were separated by filtration, yielding white crystals (103.2 g, yield 60.0%) as a target product. As such, the yield is a value based on Compound (III)-101 (Bz-HCA-NQ).

The melting point of the white crystals was 100° C.

Also, the white crystals were dissolved in a solvent, and the refractive index (x) thereof at 25° C. was calculated by Equation (1) below to be 1.645.

$$x=\{Z\times(w_1+w_2)-y\times w_2\}/w_1 \quad \text{[Equation (1)]}$$

wherein x is the refractive index of crystals; y is the refractive index of the solvent; z is the refractive index of the solution in which crystals are dissolved in the solvent: $w_1$ is the mass of the dissolved crystals; and $w_2$ is the mass of the solvent used to dissolve the crystals.

The analyzed values of elements of the obtained white crystals are shown together with theoretical values thereof Also, the theoretical values are calculated from "C35H2506P1."

Actually measured values (%) C: 73.48, H: 4.45, O: 16.79, P: 5.28

Theoretical values (%) C: 73.42, H: 4.40, O: 16.77. P; 5,41

The IR absorption spectrum data (IR data) of the obtained white crystals by a total reflection measurement method is illustrated in FIG. 1.

As is apparent from FIG. 1, the white crystals have an absorption peak which shows a phosphorus double bond (—P═O) at a wavelength of 1240 cm$^{-1}$, an absorption peak which shows a carbonyl group (C═O) at a wavelength of 1744 cm$^{-1}$, an absorption peak which shows "C═C" at a wavelength of 1632 cm$^{-1}$, absorption peaks which show "═C—H" at wavelengths of 3026 cm$^{-1}$ and 3065 cm$^{-1}$, and an absorption peak which shows "—CH$_2$—" at a wavelength of 2922 cm$^{-1}$ and also have absorption peaks which show a naphthalene ring at wavelengths of 1462 cm$^{-1}$ and 1595 cm$^{-1}$.

Also, the analyzed values (actually measured values) of elements are very similar to the theoretical values thereof.

From this, the white crystals can be confirmed to be Compound (a).

Example 2

(Preparation of Compound (b))

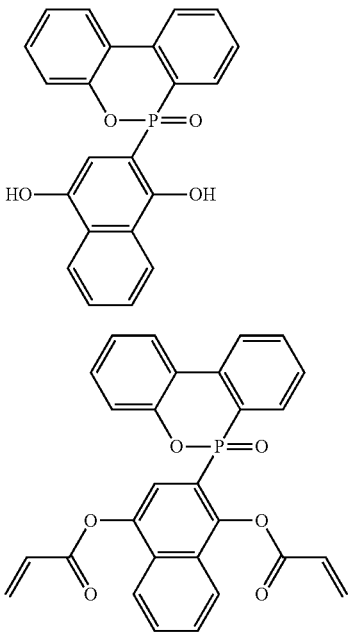

[Formula (III)-102]

[Formula (b)]

In a 1000 mL four-neck flask. Compound (III)-102 (HCA-NQ) (112.2 g, 0.30 mol) and DMAc (448.8 g, 5,2 mol) were placed and dissolved, after which acrylic acid chloride (81.9 g, 0.90 mol) having dissolved p-methoxyphenol (0.08 g, 0.006 mol) was added in a dropwise manner, and triethylamine (100.0 g, 0.99 mol) was added in a dropwise manner. Subsequently, the resulting mixture was reacted at 10° C. for 5 hrs. After termination of the reaction, the reaction solution was added into water to thus deposit crystals, and the solvent was removed, thus obtaining crude crystals. The crude crystals thus obtained were dissolved in methylisobutylketone, followed by sequentially performing water washing, dewatering, decolorization and concentrating, and the resulting concentrate was added with seed crystals to thus deposit crystals, after which the crystals were separated by filtration, yielding white crystals (95.6 g, yield 66.1%) as a target product. As such, the yield is a value based on Compound (III)-102 (HCA-NQ).

The melting point of the white crystals was 188° C.

Also, the refractive index (x) of the white crystals at 25° C. was calculated in the same manner as in Example 1 to be 1.642.

The analyzed values of elements of the obtained white crystals are shown together with theoretical values thereof Also, the theoretical values are calculated from C28H1.9O6P1.

Actually measured values (%) C: 69.84, H: 3.95, O: 19,94, P: 6.27

Theoretical values C: 69.71, H: 3.97, O: 19.90, P: 6.42

Figure 2:
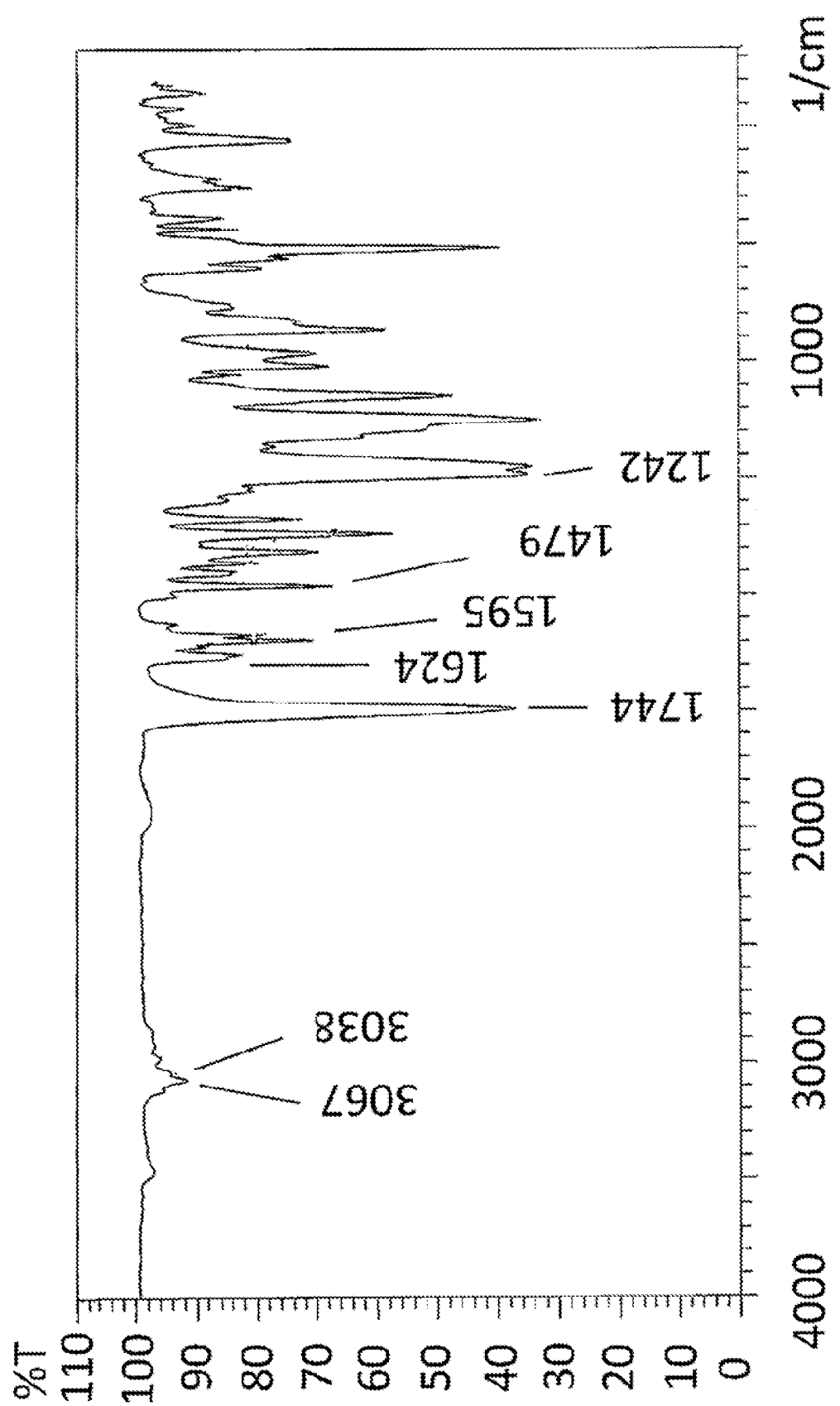
FIG. 2 illustrates IR absorption spectrum data of Compound (b) obtained in Example 2.

The IR absorption spectrum data (IR data) of the white crystals by a K.Br purification method is illustrated in FIG. 2.

As is apparent from FIG. 2, the white crystals have an absorption peak which shows a phosphorus double bond (—P=O) at a wavelength of 1242 cm$^{-1}$, an absorption peak which shows a carbonyl group (—C=O) at a wavelength of 1744 cm$^{-1}$, an absorption peak which shows "C=C" at a wavelength of 1624 cm$^{-1}$, and absorption peaks which show "=C—H" at wavelengths of 3038 cm$^{-1}$ and 3067 cm$^{-1}$, and also have absorption peaks which show a naphthalene ring at wavelengths of 1479 cm$^{-1}$ and 1595 cm$^{-1}$.

Also, the analyzed values (actually measured values) of elements are very similar to the theoretical values thereof.

From this, the white crystals can e confirmed to be Compound (b).

Example 3

(Preparation of Compound (c))

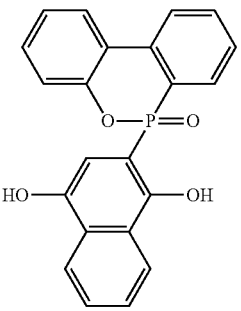

[Formula (III)-102]

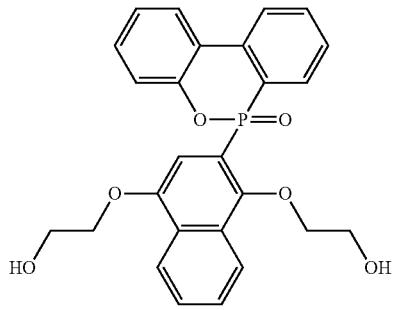

[Formula (IV)-101]

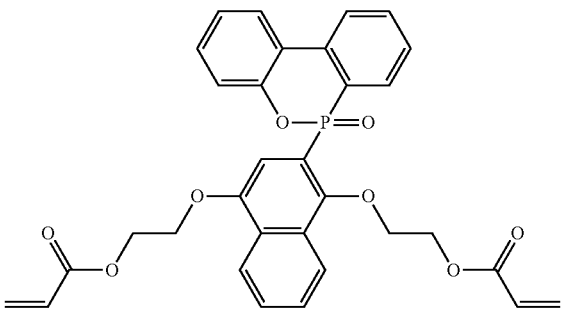

[Formula (c)]

In a 1000 mL four-neck flask, Compound (III)-102 (HCA-NQ) (299.2 g, 0.80 mol), DMAc (299.2 g, 3.4 mol), ethylene carbonate (154.9 g, 1.8 mol) and sodium carbonate (0.90 g, 0.008 mol) were placed and dissolved, and reacted at 160° C. for 8 hrs. After termination of the reaction, the reaction solution was cooled to thus deposit crystals, and the crystals were separated by filtration, thus obtaining white crystals. The white crystals thus obtained were recrystallized using benzyl acetate, yielding white crystals (304.2 g, yield 82.2%). As such, the yield is a value based on Compound (III)-102 (HCA-NQ).

The melting point of the white crystals was 205° C.

Also the refractive index (x) of the white crystals at 25° C. was calculated in the same manner as in Example 1 to be 1.661.

The obtained white crystals were Compound (IV)-101 (HCA-NQ-EO).

In a 1000 mL four-neck flask. Compound (IV)-101 (HCA-NQ-EO) (231.0 g, 0.50 mol), phenol (231.0 g. 2.5 mol), toluene (231.0 g, 2.5 mol), p-toluenesulfonic acid (18.7 g, 0.1 mol) and p-methoxyphenol (0.1 g, 0.0008 mol) were placed and dissolved, and the internal pressure of the flask was adjusted to about 40 kPa at 100° C. so that toluene was refluxed, after which acrylic acid (93.6 g, 1.3 mol) was added in a dropwise manner, and reaction was carried out for 11 hrs while water produced by the reaction was removed outside the reaction system. After termination of the reaction, water washing, dewatering, decolorization and concentrating were sequentially performed, and the obtained concentrate was added with seed crystals to thus deposit crystals, after which the crystals were separated by filtration, yielding white crystals (207.3 g, yield 72.7%) as a target product. As such, the yield is a value based on Compound (IV)-101 (HCA-NQ-EO).

The melting point of the white crystals was 115° C.

Also, the refractive index (x) of the white crystals at 25° C. was calculated in the same manner as in Example 1 to be 1.616.

The analyzed values of elements of the obtained white crystals are shown together with theoretical values thereof. Also, the theoretical values are calculated from C:32H27O8P1.

Actually measured values (%) C: 67.63, H: 4.71, O: 22.32, P: 5.34

Theoretical values (%) C: 67.37, H: 4.77, O: 22.43, P: 5.43

Figure 3:
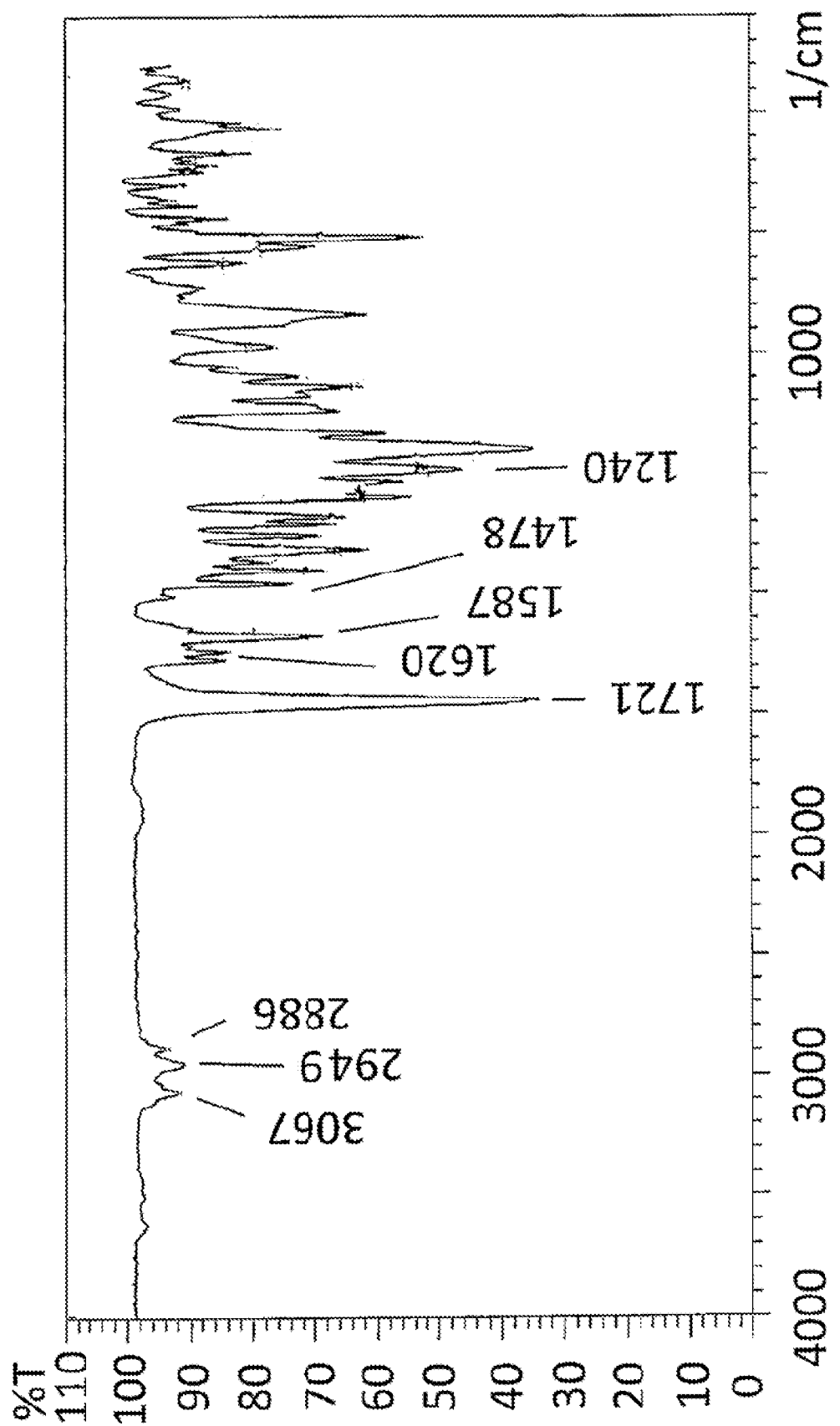
FIG. 3 illustrates IR absorption spectrum data of Compound (c) obtained in Example 3.

The IR absorption spectrum data (IR data) of the obtained white crystals by a KBr purification method is illustrated in FIG. 3.

As is apparent from FIG. 3, the white crystals have an absorption peak which shows a phosphorus double bond (—P═O) at a wavelength of 1240 $cm^{-1}$, an absorption peak which shows a carbonyl group (C═O) at a wavelength of 1721 $cm^{-1}$ an absorption peak which shows "C═C" at a wavelength of 1620 $cm^{-1}$, an absorption peak which shows "═C—H" at a wavelength of 3067 $cm^{-1}$, and absorption peaks which show "—CH$_2$—" at wavelengths of 2886 $cm^{-1}$ and 2949 $cm^{-1}$, and also have absorption peaks which show a naphthalene ring at wavelengths of 1478 $cm^{-1}$ and 1587 $cm^{-1}$.

Also, the analyzed values (actually measured values) of elements are very similar to the theoretical values thereof.

From this, the obtained white crystals can be confirmed to be Compound (c).

As described hereinbefore, the present invention provides a phosphorus-based (meth)acrylate compound and a method of preparing the same. According to the present invention, a novel compound having high refractive index adapted for use in optical resin materials, etc., without containing a sulfur atom, and a method of preparing the same are provided.

The present invention is useful in material fields requiring high refractive index, including optical resin materials, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A phosphorus-based (meth)acrylate compound represented by Formula (I) below:

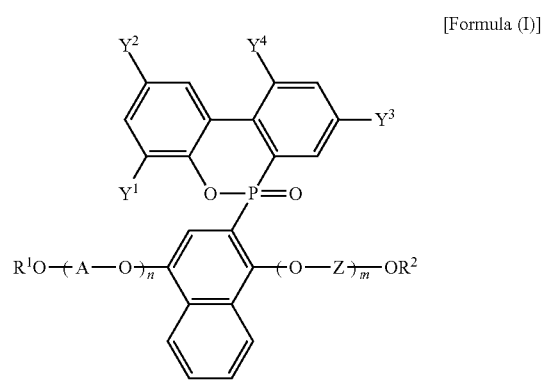

[Formula (I)]

wherein $Y^1$ is an aralkyl group; and $Y^2$, $Y^3$ and $Y^4$ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; n and m are each independently 0, 1 or 2, and when n or m is 2, two As or Zs are the same as or different from each other; and $R^1$ and $R^2$ are each independently a hydrogen atom or a (meth)acryloyl group, in which at least one of $R^1$ and $R^2$ is a (meth)acryloyl group.

2. The phosphorus-based (meth)acrylate compound of claim 1, which is represented by Formula (a) below:

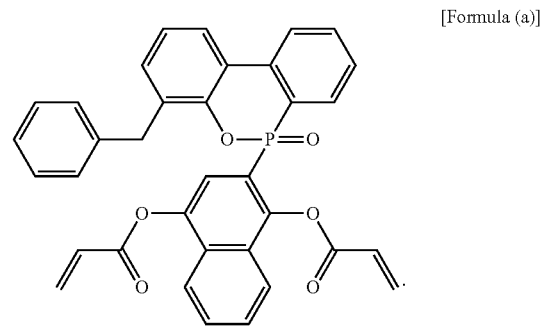 [SMILES: C=CC(=O)Oc1cc(P2(=O)Oc3c(Cc4ccccc4)cccc3-c3ccccc32)c(OC(=O)C=C)c2ccccc12]

[Formula (a)]

3. A method of preparing a phosphorus-based (meth)acrylate compound represented by Formula (I)-1 below, comprising:

reacting a compound represented by Formula (III) below with one or more selected from the group consisting of (meth)acrylic acid, (meth)acrylic acid chloride and di(meth)acrylic acid anhydride to give a phosphorus-based (meth)acrylate compound represented by Formula (I)-1 below:

[Formula (III)]

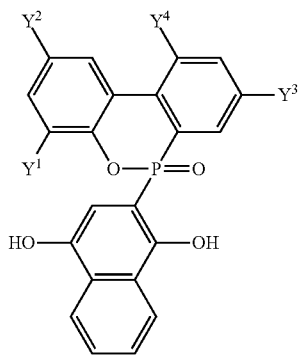

[Formula (I)-1]

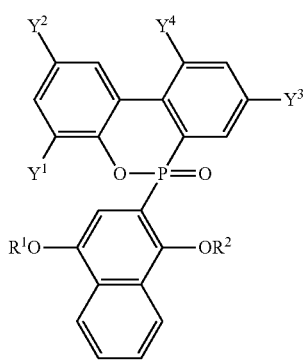

wherein Y¹ is an aralkyl group; and

Y², Y³ and Y⁴ are each independently a hydrogen atom, a halogen atom, a nitro group, an amino group, a carboxyl group, a hydroxyl group, an alkyl group, an aryl group, an aralkyl group, an acyl group or an allyl group; and R¹ and R² are each independently a hydrogen atom or a (meth)acryloyl group, in which at least one of R¹ and R² is a (meth)acryloyl group.

4. A method of preparing a phosphorus-based (meth)acrylate compound represented by Formula (I)-2 below, comprising:

reacting a compound represented by Formula (III) below with one or more selected from the group consisting of ethylene oxide, ethylene carbonate, propylene oxide and propylene carbonate to give a compound represented by Formula (IV) below; and reacting the compound represented by Formula (IV) below with one or more selected from the group consisting of (meth)acrylic acid, (meth)acrylic acid chloride and di(meth)acrylic acid anhydride to give a phosphorus-based (meth)acrylate compound represented by Formula (I)-2 below:

[Formula (III)]

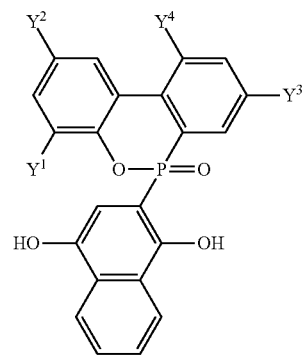

[Formula (IV)]

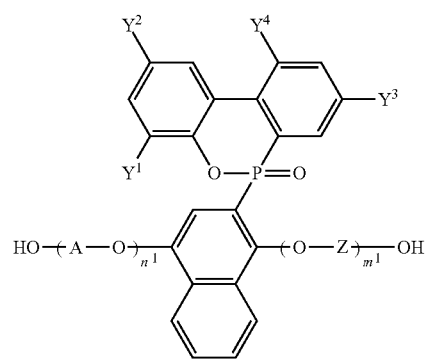

[Formula (I)-2]

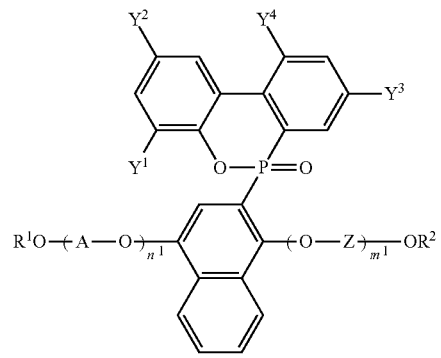

wherein Y¹ is an aralkyl group; and

Y², Y³ and Y⁴ are each independently a hydrogen atom, a halogen atom, a nitro group, an amino group, a carboxyl group, a hydroxyl group, an alkyl group, an aryl group, an aralkyl group, an acyl group or an allyl group; A and Z are each independently an ethylene group or an isopropylene group; n¹ and m¹ are each independently 0, 1 or 2, in which both of n¹ and m¹ are not zero, and when n¹ or m¹ is 2, two As or Zs are the same as or different from each other; and R¹ and R² are each independently a hydrogen atom or a (meth)acryloyl group, in which at least one of R¹ and R² is a (meth)acryloyl group.

* * * * *